US008334518B2

(12) United States Patent
Matsuda et al.

(10) Patent No.: US 8,334,518 B2
(45) Date of Patent: Dec. 18, 2012

(54) DRINKING WATER SERVER

(75) Inventors: Masaaki Matsuda, Hyogo (JP); Hidehiro Takano, Hyogo (JP); Takao Morigaki, Hyogo (JP)

(73) Assignee: Noritz Corporation, Hyogo (JP)

( * ) Notice: Subject to any disclaimer, the term of this patent is extended or adjusted under 35 U.S.C. 154(b) by 295 days.

(21) Appl. No.: 12/733,846

(22) PCT Filed: Sep. 26, 2008

(86) PCT No.: PCT/JP2008/068010
§ 371 (c)(1),
(2), (4) Date: Mar. 24, 2010

(87) PCT Pub. No.: WO2009/041740
PCT Pub. Date: Apr. 2, 2009

(65) Prior Publication Data
US 2010/0200769 A1 Aug. 12, 2010

(30) Foreign Application Priority Data
Sep. 28, 2007 (JP) ................................ 2007-253225

(51) Int. Cl.
*A61L 2/10* (2006.01)
*G01N 21/01* (2006.01)

(52) U.S. Cl. .................... 250/436; 250/435; 250/432 R; 210/94; 210/97

(58) Field of Classification Search .................. 250/436; 210/181, 94; 222/113
See application file for complete search history.

(56) References Cited

U.S. PATENT DOCUMENTS

| | | | | |
|---|---|---|---|---|
| 4,757,921 | A | 7/1988 | Snowball | |
| 6,139,726 | A * | 10/2000 | Greene | 210/94 |
| 6,483,119 | B1 * | 11/2002 | Baus | 250/436 |
| 2002/0046569 | A1 * | 4/2002 | Faqih | 62/188 |
| 2004/0129723 | A1 * | 7/2004 | Meder et al. | 222/113 |
| 2006/0059922 | A1 * | 3/2006 | Anderson et al. | 62/93 |

(Continued)

FOREIGN PATENT DOCUMENTS

JP 61-194862 U 12/1986

(Continued)

OTHER PUBLICATIONS

International Search Report mailed on Nov. 18, 2008.

*Primary Examiner* — Nikita Wells
*Assistant Examiner* — Johnnie L Smith
(74) *Attorney, Agent, or Firm* — Rader, Fishman & Grauer PLLC

(57) ABSTRACT

The invention presents a drinking water server having a configuration capable of suppressing generation of bacteria in a cold water tank, in a cold water pour tube, and in a pour valve. An opening part (2*c*) is formed in bottom side of a cold water tank (2), and a straight cold water pour tube (6) disposed horizontally in this opening part (2*c*) by way of a bent part (6*b*). An ultraviolet lamp (8) is disposed so as to reach up to a bottom part of the bent part (6*b*) by way of the opening part (2*c*) from inside of the cold water tank (2), so that ultraviolet rays emitted from the ultraviolet lamp (8) may be emitted uniformly both in the cold water tank (2) and in the duct of the cold water pour tube (6). As a valve body of a cold water pour valve (7), a diaphragm (71) for clogging the leading end of the cold water pour tube (6) is used, and dead angle of ultraviolet rays is eliminated.

5 Claims, 6 Drawing Sheets

U.S. PATENT DOCUMENTS

| | | | | |
|---|---|---|---|---|
| 2007/0075006 | A1* | 4/2007 | Watanabe et al. | 210/181 |
| 2007/0175063 | A1* | 8/2007 | Morgan et al. | 34/467 |

FOREIGN PATENT DOCUMENTS

| | | | |
|---|---|---|---|
| JP | 62-282687 | A | 12/1987 |
| JP | 63-238161 | A | 10/1988 |
| JP | 10-151464 | A | 6/1998 |
| JP | 10-339539 | A | 12/1998 |
| JP | 2005-350067 | A | 12/2005 |
| JP | 2006-213335 | A | 8/2006 |

* cited by examiner

DRINKING WATER SERVER

TECHNICAL FIELD

The present invention relates to a drinking water server, and more particularly to a drinking water server capable of heating or cooling the drinking water supplied from a detachable water bottle, and taking out from a pour port.

BACKGROUND ART

FIG. 5 shows an outline configuration of a conventional drinking water server. As shown in the diagram, the drinking water server of this type is composed to store the drinking water supplied form a water bottle (a) filled with drinking water temporarily in a hot water tank (b) provided with a heater (h) and in a cold water tank (c) provided with a cooler (not shown). Pour tubes (d), (e) for taking out the drinking water are connected to the tanks (b), (c), and pour valves (f), (g) are provided at the leading ends of the pour tubes (d), (e).

In the case of such configuration of temporary storage of drinking water in the tanks (b), (c), it is necessary to prevent growth of bacteria in the tanks (b), (c), and in the drinking water server of this type, therefore, as shown in the drawing, it was proposed to stock the drinking water supplied from the water bottle (a) once in the hot water tank (b) by way of a drinking water feed tube (i), and sterilize by heat in the hot water tank (b), and feed into the cold water tank (c) by way of a second drinking water feed tube (j) (see, for example, Japanese Patent Application Laid-Open No. 2006-347556).

However, even in this case of sterilizing the drinking water supplied into the cold water tank (c) by heat, bacteria may grow in the cold water tank (c). Accordingly, in the conventional drinking water server, it was proposed to sterilize in the cold water tank (c) by providing the cold water tank (c) with an ultraviolet lamp (k) for emitting ultraviolet rays (see, for example, Japanese Patent Application Laid-Open No. 2006-62720). It was also proposed to install an ultraviolet lamp closely to the pour valve (g) for pouring cold water (within the pour tube (e)), not inside the cold water tank (c)) (see, for example, Japanese Patent Application Laid-Open No. 2000-128292).

However, the conventional configurations had the following problems, and improvements have been desired.

That is, in the configuration of installing an ultraviolet lamp closely to the pour valve (g) for pouring cold water, bacteria may grow inside the cold water tank (c), and the tank wall may be slimy. Also, in the configuration of installing an ultraviolet lamp in the cold water tank (c), ultraviolet rays are not emitted into the inside of the pour tube (e) of cold water, and bacteria may grow in the pour tube (e).

Moreover, in the conventional drinking water server, the electromagnetic valve used as the pour valve (g) is designed to close a valve body (m) by making use of water pressure in the pour tube (e) as shown in FIG. 6, and if the valve body (m) is kept closed, a large amount of water may circulate and stay in a rear part (n) of the valve body (m). As a result, bacteria may grow in the rear part (n) of the valve body (m).

The present invention is devised in the light of such problems, and it is hence a primary object thereof to present a drinking water server having a structure capable of suppressing generation of bacteria in the cold water tank of the drinking water server, in the cold water pour tube, and in the pour valves.

SUMMARY OF THE INVENTION

To achieve the object, the drinking water server of the present invention is a drinking water server including a cold water pour piping for taking out cold water disposed by communicating with an opening part formed in a cold water tank, and a cold water pour valve disposed at a leading end of the cold water pour piping, in which ultraviolet emitting means for emitting ultraviolet rays into the cold water tank is disposed oppositely to the opening part, and a duct of the cold water pour piping is formed straightly, and a diaphragm type valve body for clogging the leading end of the cold water pour piping is used as a valve body for the cold water pour valve.

That is, in the present invention, since the ultraviolet emitting means for emitting ultraviolet rays into the cold water tank is disposed oppositely to the opening part communicating with the cold water pour piping in the cold water tank, and the duct of the cold water pour piping is formed straightly, for example, when the opening part is formed in a side face of the cold water tank, ultraviolet rays are emitted both into the cold water tank and into the duct of the cold water pour piping by the ultraviolet emitting means, and therefore generation of bacteria both in the cold water tank and the duct can be suppressed by one ultraviolet emitting means. Moreover, as the valve body of the cold water pour valve, a diaphragm type valve body (diaphragm) for closing the leading end of the cold water pour piping is used, unlike the conventional drinking water server, the water does not stay in the rear part of the valve body, and generation of bacteria in the cold water pour valve can be suppressed.

In a second drinking water server of the present invention, the opening part is formed in the bottom side of the cold water tank, and the cold water pour piping communicating with this opening part is disposed horizontally or obliquely downward by way of a bent part, and the ultraviolet emitting means is disposed to reach the bottom side of the bent part from the inside of the cold water tank by way of the opening part.

That is, in the cold water tank, an outlet (the opening part) of drinking water in the cold water tank is preferred to be formed in a lower part of the cold water tank as far as possible in consideration of discharge property or the like of the drinking water in the cold water tank, and hence in the second drinking water server of the present invention, the opening part of the cold water tank is formed in the bottom side of the cold water tank, and a bent part is formed in the cold water pour piping, and by way of this bent part, the cold water pour piping is disposed straightly, either horizontally or obliquely downward. The ultraviolet emitting means is disposed to reach the bottom side of the bent part from the inside of the cold water tank by way of the opening part, and ultraviolet rays emitted from the ultraviolet emitting means are emitted both into the cold water tank and into the duct of the cold water pour piping. Therefore, generation of bacteria both in the cold water tank and the duct can be suppressed by one ultraviolet emitting means.

In a third drinking water server of the present invention, the ultraviolet emitting means is composed of a bar-shaped ultraviolet lamp, and an ultraviolet lamp insertion port is provided in the bottom side of the bent part.

That is, in the third drinking water server of the present invention, by inserting the bar-shaped ultraviolet lamp from the ultraviolet lamp insertion port provided in the bottom side of the bent part of the cold water pour piping, the ultraviolet lamp can be mounted and exchange, and the ultraviolet lamp can be mounted or exchanged easily. In particular, in the drinking water server of this type, usually, the hot water tank is disposed beneath the cold water tank, and between the bottom side of the cold water tank and the bottom side of the floor on which the drinking water server is installed, at least a gap is formed for the portion of the height of the hot water tank, and the ultraviolet lamp can be exchanged easily without stooping or leaning the body, and the exchange work is easily. Herein, the bar-shaped ultraviolet lamp includes an ultraviolet lamp of straight tube type, an ultraviolet lamp of U-bent tube formed like a bar, and others.

In a fourth drinking water server of the present invention, the diaphragm type valve body is disposed oppositely to the ultraviolet emitting means.

That is, in the fourth drinking water server of the present invention, since the diaphragm type valve body closing the leading end of the cold water pour piping is disposed oppositely to the ultraviolet emitting means, there is not dead angle for emission of ultraviolet rays from the ultraviolet emitting means to the cold water pour valve in the cold water pour piping, and generation of bacteria in these areas can be securely prevented.

In a fifth drinking water server of the present invention, the diaphragm type valve body has a resistance to ultraviolet rays at least in a portion opposite to the ultraviolet emitting means.

That is, in the fifth drinking water server of the present invention, since at least the portion opposite to the ultraviolet emitting means has a resistance to ultraviolet rays, trouble of cold water pour valve due to deterioration of the valve body by exposure to ultraviolet rays can be prevented for a long period.

PREFERRED EMBODIMENTS FOR CARRYING OUT THE INVENTION

Preferred embodiments of the present invention are described specifically below by reference to the accompanying drawings.

Preferred Embodiment 1

Figure 1:
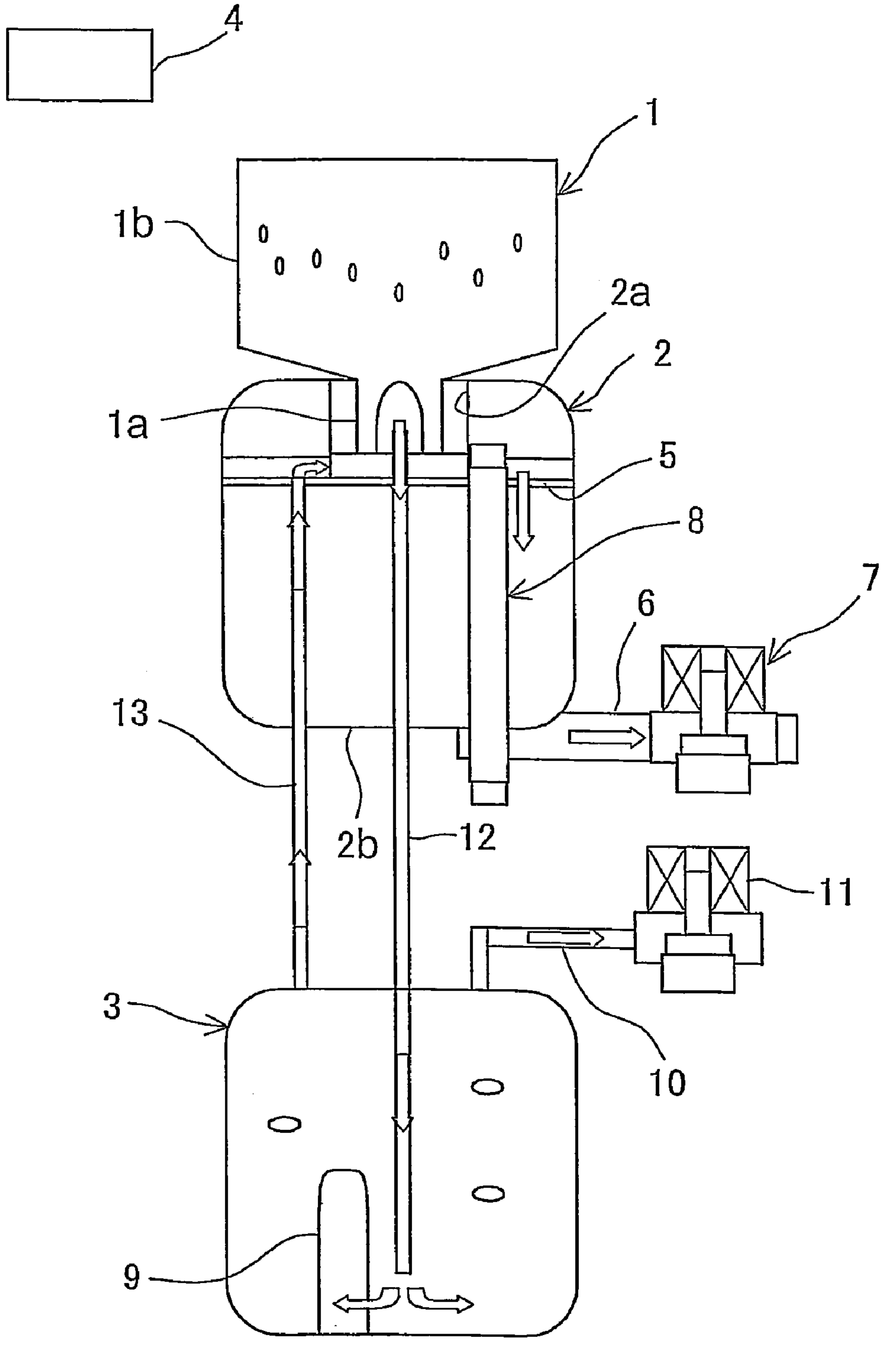
FIG. 1 is an outline configuration diagram showing an example of a drinking water server of the present invention.

FIG. 1 shows an example of an outline configuration of a drinking water server of the present invention. The drinking water server of the present invention is a drinking water server configured to sterilize both the cold water tank and the cold water take-out path by using one ultraviolet emitting means, and as shown in the drawing, it mainly includes a water bottle 1, a cold water tank 2, a hot water tank 3, a control unit (control means) 4, and an ultraviolet lamp (ultraviolet emitting means) 8.

The water bottle 1 is filled with drinking water to be supplied into the drinking water server, and is an exchangeable container. The water bottle 1 is provided with a pour port 1*a* for supplying the contained drinking water into the drinking water server, projecting from its shell part 1*b*, and this pour port 1*a* is sealed by a cap or the like before being connected to the drinking water server. That is, this water bottle 1 is presented in a state of the contained drinking water free from being contamination by bacteria. When being connected to the drinking water server, the pour port 1*a* is unsealed, and the bottle is installed at a specified position of the drinking water server (in a recess 2*a* of the cold water tank 2 specifically as described below) so that the pour port 1*a* may be positioned downward.

The cold water tank 2 is a metal tank having the recess 2*a* formed in the upper part so that the water bottle 1 may be mounted. In the bottom side of this recess 2*a*, one end of a drinking water feeding pipe 12 is provided for feeding the drinking water supplied from the water bottle 1 into the hot water tank 3 (the detail is described below).

This cold water tank 2 is provided with a cooler (not shown) for cooling the drinking water by a refrigerant supplied from a compressor not shown. The cooler is controlled by the control unit 4. That is, the control unit 4 controls the operation of the cooler so that the temperature of the drinking water in the cold water tank 2 may be maintained at a prescribed temperature, on the basis of the temperature detection signal obtained from a temperature sensor (not shown) for measuring the temperature of the drinking water in the cold water tank 2. This cold water tank 2 has its surrounding thermally insulated by an insulating material (not shown) so that the drinking water cooled by the cooler may not be warmed by an ambient temperature.

In the inner upper part of the cold water tank 2, a baffle plate 5 is disposed so that the drinking water of high temperature supplied from a second drinking water feed tube 13 mentioned below may not be mixed directly with the drinking water of low temperature in the tank (the drinking water cooled by the cooler), and the drinking water supplied from the second drinking water feed tube 13 is mixed slowly with the drinking water of low temperature by way of a through-hole (not shown) provided in this baffle plate 5.

A cold water pour tube (cold water pour piping) 6 is connected to this cold water tank 2 for taking out the drinking water in the tank 2, and a cold water pour valve 7 is connected to the leading end of the cold water pour tube 6. That is, by opening this cold water pour valve 7, the drinking water in the cold water tank 2 can be taken out.

Figure 2:
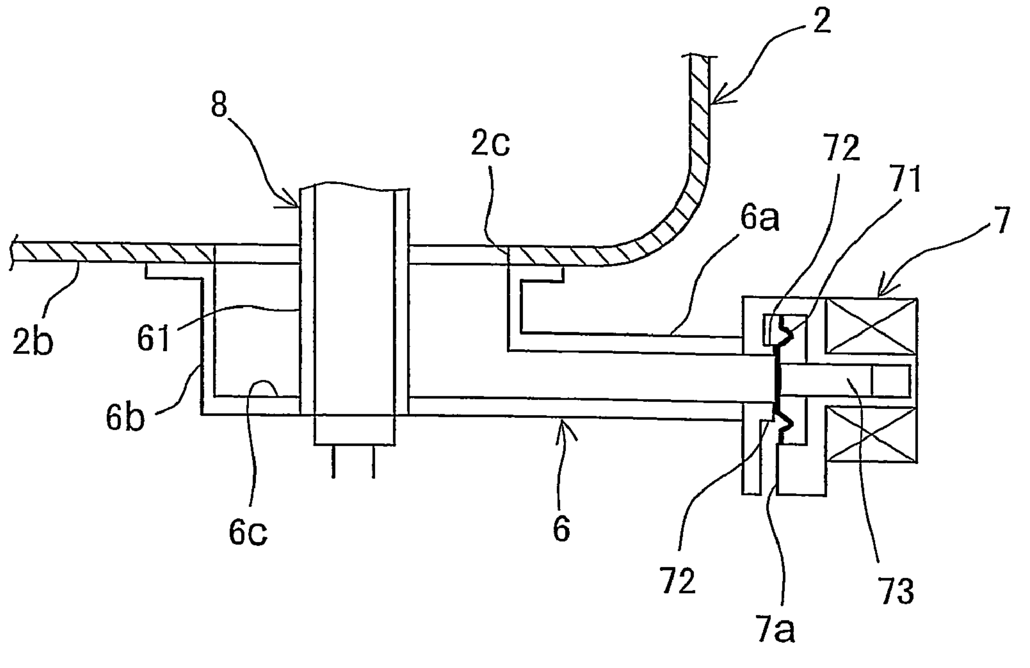
FIG. 2 is a partially magnified view showing a connection state of a cold water tank and a cold water pour tube in the drinking water server.

Herein, the cold water pour tube 6 is connected to the bottom side 2*b* of the cold water tank 2 in the preferred embodiment, as shown in FIG. 2, in consideration of ease of discharge of drinking water from the tank as well as uniform arrangement of position with a hot water pour tube 10 for taking out the drinking water from the hot water tank 3 described below. More specifically, an opening part 2*c* for connecting the cold water pour tube 6 is formed in the bottom side 2*b* of the cold water tank 2, and the cold water pour tube 6 is connected so as to communicate with this opening part 2*c*.

This cold water pour tube 6 has, as shown in the drawing, a duct main body 6*a* having a straight duct, and a bent part 6*b* for connecting this duct main body 6*a* to the opening part 2*c*. The bent part 6*b* has its end part at the opposite side to the duct main body 6*a* connected to the opening part 2*c*, and it is a member for shifting the direction of the duct so that the duct main body 6*a* may be horizontal (or obliquely downward), and in this preferred embodiment, together with the duct main body 6*a*, it is made of SUS or other metal (in the present preferred embodiment, since the duct main body 6*a* is disposed horizontally, the bent part 6*b* is formed to bend the duct by 90 degrees).

In the bottom side 6*c* of this bent part 6*b*, at a position corresponding to the opening part 2*c*, an ultraviolet lamp insertion pipe 61 is provided in upright position. This ultraviolet lamp insertion pipe 61 is a hollow tubular member for inserting the ultraviolet lamp 8, and is a transparent or translucent container for passing ultraviolet rays emitted from the ultraviolet lamp 8 in a state having the ultraviolet lamp 8 being inserted in the insertion pipe 61.

More specifically, the ultraviolet lamp insertion pipe 61 is disposed so as to be orthogonal to the extension direction of the duct main body 6*a* (specifically in the horizontal direction), so that the ultraviolet rays may be emitted into the duct of the duct main body 6*a* by the ultraviolet lamp 8 when the ultraviolet lamp 8 is installed in the ultraviolet lamp insertion pipe 61.

The lower end of the ultraviolet lamp insertion pipe 61 is opened to the lower side of the cold water pour tube 6, and through this opening part, the ultraviolet lamp 8 can be put in and out of the insertion pipe 61. In the example shown in FIG. 2, the lower end of the ultraviolet lamp insertion pipe 61 is flush with the outer wall of the bottom side 6*c* of the bent part 6*b* of the cold water pour tube 6, but as shown in FIG. 1, it may be composed to project from the bottom side 6*c*. Essentially, when the ultraviolet lamp 8 is inserted in the ultraviolet lamp insertion pipe 61, in the ultraviolet lamp 8, the position for emitting ultraviolet rays may be positioned so as to reach at least the duct bottom side of the cold water pour tube 6, and the ultraviolet rays emitted from the ultraviolet lamp 8 may be emitted, without leak, into the duct bottom side of the cold water pour tube 6.

On the other hand, the upper end of the ultraviolet lamp insertion pipe 61 sealed, and at least its upper end is composed to reach up to the baffle plate 5 as shown in FIG. 1. Herein, the upper end of the ultraviolet lamp insertion pipe 61 is composed to reach up to the baffle plate 5 in order that the ultraviolet rays emitted from the ultraviolet lamp 8 inserted in the ultraviolet lamp insertion pipe 61 may be emitted at least entirely in the inside of the tank (the cold water storing portion) of the baffle plate 5. Therefore, it is also possible to emit ultraviolet rays to the upper parts of the baffle plate 5 by raising the position of the upper end of the ultraviolet lamp insertion pipe 61.

The cold water pour valve 7 is provided at the leading end of the duct main body 6*a* of the cold water pour tube 6 as mentioned above, and in the present invention, in this cold water pour valve 7; a diaphragm type valve body (diaphragm) 71 is used as a valve body for closing the leading end of the duct main body 6*a*.

Specifically, this cold water pour valve 7 has a valve seat 72 formed along the extension of the duct main body 6*a*, and the diaphragm 71 is disposed to contact with or depart from this valve seat 72. In the rear part of this diaphragm 71, a plunger 73 is provided, and as this plunger 73 advances, the diaphragm 71 closes the duct main body 6*a*, and as the plunger 73 retreats, the closed state of the duct main body 6*a* is released, so that the drinking water in the duct main body 6*a* may be guided into the pour port 7*a*.

In other words, in this preferred embodiment, the cold water pour valve 7 having the diaphragm type valve body is disposed laterally to be orthogonal to the cold water pour tube 6 disposed horizontally, and the diaphragm 71 is disposed to be opposite to the ultraviolet lamp 8 described below. This diaphragm 71 is composed of a member of high resistance to ultraviolet rays, such as fluorine resin (or is coated with a fluorine resin having a resistance to ultraviolet rays), and at least the portion facing the ultraviolet lamp 8 is composed to have a resistance to ultraviolet rays.

The ultraviolet lamp 8 is provided for the purpose of sterilizing the drinking water in the cold water tank 2 and in the duct of the cold water pour tube 6, and in this preferred embodiment, it is a lamp of a bar shape that can be inserted into the ultraviolet lamp insertion pipe 61, being capable of emitting ultraviolet rays radially to the surrounding. More specifically, such ultraviolet lamp is preferably a lamp of so-called straight tube type, and other examples include U-shape ultraviolet lamp and others that can be inserted into the ultraviolet lamp insertion pipe 61. The ultraviolet lamp 8 is controlled by the control unit 4 to light or extinguish.

The hot water tank 3 is a metal tank disposed beneath the cold water tank 2. This hot water tank 3 is provided with an electric heater (heating means) 9 for heating the drinking water in the tank. This electric heater 9 is, same as the cooler of the cold water tank 2, controlled by the control unit 4. That is, the control unit 4 controls on/off of the electric heater 9 so that the drinking water in the hot water tank 3 may be maintained at a prescribed temperature on the basis of the temperature detection signal obtained from a temperature sensor (not shown) for measuring the temperature of the drinking water in the hot water tank 3.

The hot water tank 3 is thermally insulated with its surrounding covered with an insulating material (not shown) so that the drinking water heated by the electric heater 9 may not be cooled easily by natural heat release.

In the upper part of the hot water tank 3 (on the top of the hot water tank 3 in the illustrated example), a hot water pour tube 10 is connected for taking out the drinking water in the hot water tank 3, and a hot water pour valve 11 is attached to the leading end of this hot water pour tube 10. That is, by opening this hot water pour valve 11, the drinking water of the hot water tank 3 can be taken out.

In the drinking water server having such configuration, the drinking water supplied from the water bottle 1 is once guided into the hot water tank 3, and is heated (sterilized by heat) in this hot water tank 3, and then supplied into the cold water tank 2.

That is, a drinking water feed tube 12 has its one end disposed oppositely to the recess 2*a* of the cold water tank 2, and other end disposed to be guided into the tank (in particular, near the bottom side of the tank) of the hot water tank 3 as shown in the drawing. In other words, the hot water tank 3 is configured so that the drinking water may be supplied from the water bottle 1 by way of the drinking water feed tube 12.

When the drinking water in the cold water tank 2 is poured out from the cold water pour tube 6, or when there is no drinking water at the downstream side of the water bottle 1 (when the tanks 2, 3 are empty, for example, at the time of installation of the drinking water server), the drinking water in the water bottle 1 drops spontaneously by way of the drinking water feed tube 12, and flows into the hot water tank 3, and the drinking water in the hot water tank 3 is supplied into the cold water tank 2 by way of a second drinking water feed tube 13. This second drinking water feed tube 13 has its one end connected to the upper part of the hot water tank 3, and other end disposed oppositely to the upper side of the baffle plate 5 in the cold water tank 2, and the drinking water guided into the upper side of the baffle plate 5 in the cold water tank 2 by way of the second drinking water feed tube 13 is supplied into the cold water tank 2 by way of a through-hole (not shown) of the baffle plate 5.

The control unit 4 is a control device for controlling the parts of the drinking water server, and includes a microcomputer not shown. The microcomputer stores a program for executing the control to maintain the drinking water in the cold water tank 2 and the hot water tank 3 at a prescribed temperature by controlling the cooler and the electric heater 9.

In the drinking water server having such configuration, sterilization in the cold water tank 2 and the cold water pour tube 6 is specifically described below.

That is, in drinking water server of the present preferred embodiment, as mentioned above, the ultraviolet lamp 8 is provided in order to sterilize in the cold water tank 2 and the cold water pour tube 6. This ultraviolet lamp 8 is illuminated all the time or occasionally (for example, periodically by the control of the control unit 4), and by lighting the ultraviolet lamp 8, the inside of the cold water tank 2 and the cold water pour tube 6 is sterilized.

More specifically, in this preferred embodiment, the bar-shaped ultraviolet lamp 8 inserted in the ultraviolet lamp insertion pipe 61 is disposed so as to penetrate the tube from the bottom side 2*b* of the cold water tank 2 to the baffle plate 5, and this ultraviolet lamp 8 emits ultraviolet rays radially to the surrounding, and the inside of the cold water tank 2 (especially the tank beneath the baffle plate 5) is entirely irradiated with ultraviolet rays by this ultraviolet lamp 8. As a result, the inside of the cold water tank 2 is sterilized.

On the other hand, the cold water pour tube 6 is disposed so that the lower end side of the ultraviolet lamp 8 may reach up to the duct bottom side of the cold water pour tube 6 by penetrating through the opening part 2*c* of the cold water tank 2, and the duct main body 6*a* disposed in a direction orthogonal to the ultraviolet lamp 8 has a straight duct, so that the ultraviolet rays emitted from the ultraviolet lamp 8 may be emitted uniformly to the inside (duct) of the duct main body 6*a* and the bent part 6*b*. Moreover, in the present preferred embodiment, since a diaphragm 71 is used as a valve body for closing the leading end of the duct main body 6*a*, water is not staying in the rear part of this diaphragm 71, and there is no dead angle of emission of ultraviolet rays in the duct of the duct main body 6*a*, so that the inside of the cold water pour tube 6 can be sterilized securely.

Preferred Embodiment 2

Figure 3:
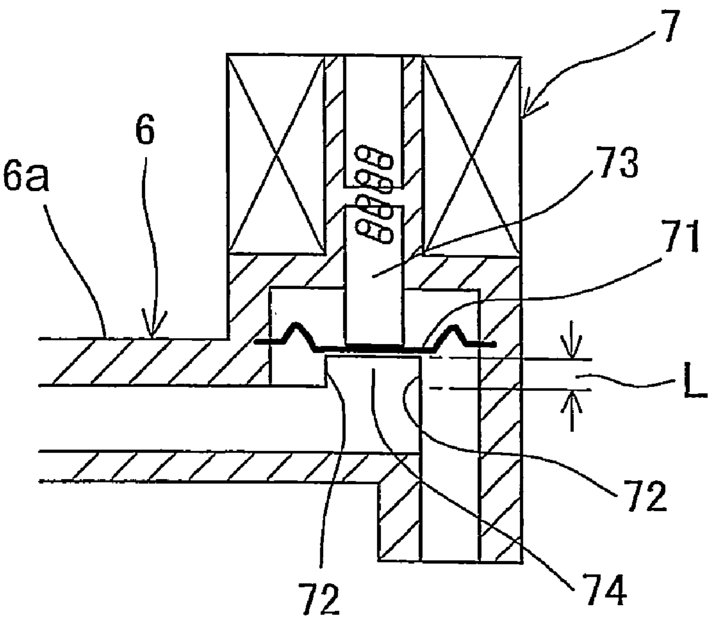
FIG. 3 is an explanatory diagram showing a preferred embodiment changed in the layout of a cold water pour valve in the drinking water server.

Referring next to FIG. 3, preferred embodiment 2 of the present invention is specifically described below. Preferred embodiment 2 is similar to preferred embodiment 1 except that the cold water pour valve 7 is disposed in a vertical direction instead of the lateral direction, and hence the leading end of the duct main body 6*a* is bent upward. The other configuration is same as in preferred embodiment 1, and the common parts are identified with same reference numerals, and the explanation is omitted.

In this case, therefore, the leading end of the duct main body 6*a* is bent upward by 90 degrees, and a valve seat 72 is formed, and a diaphragm 71 is disposed to contact with this valve seat 72. When the cold water pour valve 7 is composed in this manner, as shown in FIG. 3, there is a dead angle of the ultraviolet lamp 8 in a leading end part (bent space) 74 of the duct main body 6*a*, and it is not preferable as compared with preferred embodiment 1, but it is advantageous as compared with the prior art because water is not staying in the rear part of the valve body.

The present applicant experimented about the configuration shown in FIG. 3 under the condition specified above, and discovered that, in the case of the duct diameter of the duct main body 6*a* of 6 mm, the general bacterial count of 100 cfu/ml or less (the tap water quality standard in Japan) can be satisfied when the height L of the valve seat 72 is 1.5 mm or less. Further, when the height L of the valve seat 72 is set at 0.5 mm or less, the dead angle of ultraviolet rays is decreased, it is found that the bactericidal effects by ultraviolet rays can be obtained.

Therefore, in the present invention, by specifying the height L of the valve seat 72 with a numerical value, when the pour valve 7 is disposed in a vertical direction, same effects as in a lateral direction can be obtained.

Preferred Embodiment 3

Figure 4:
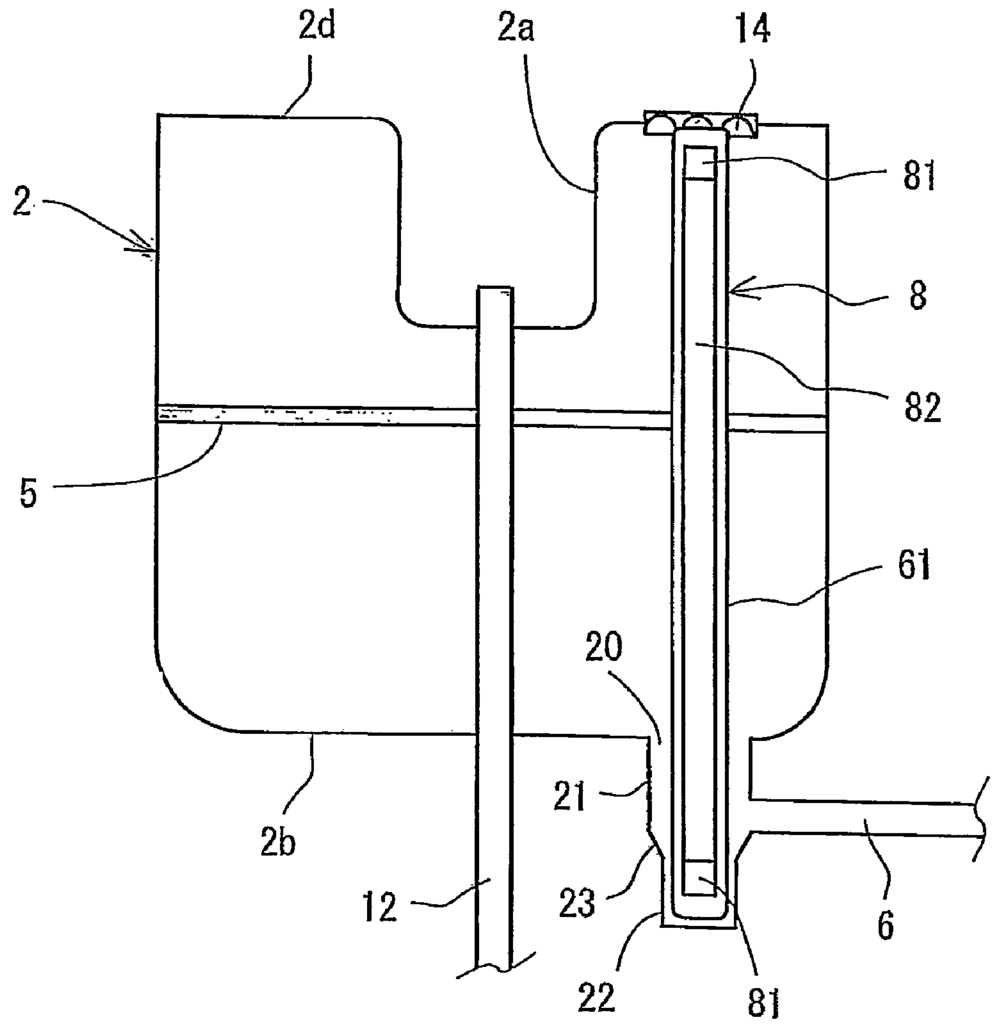
FIG. 4 is an explanatory diagram showing a preferred embodiment changed in the mounting state of an ultraviolet lamp in the drinking water server.
Figure 5:
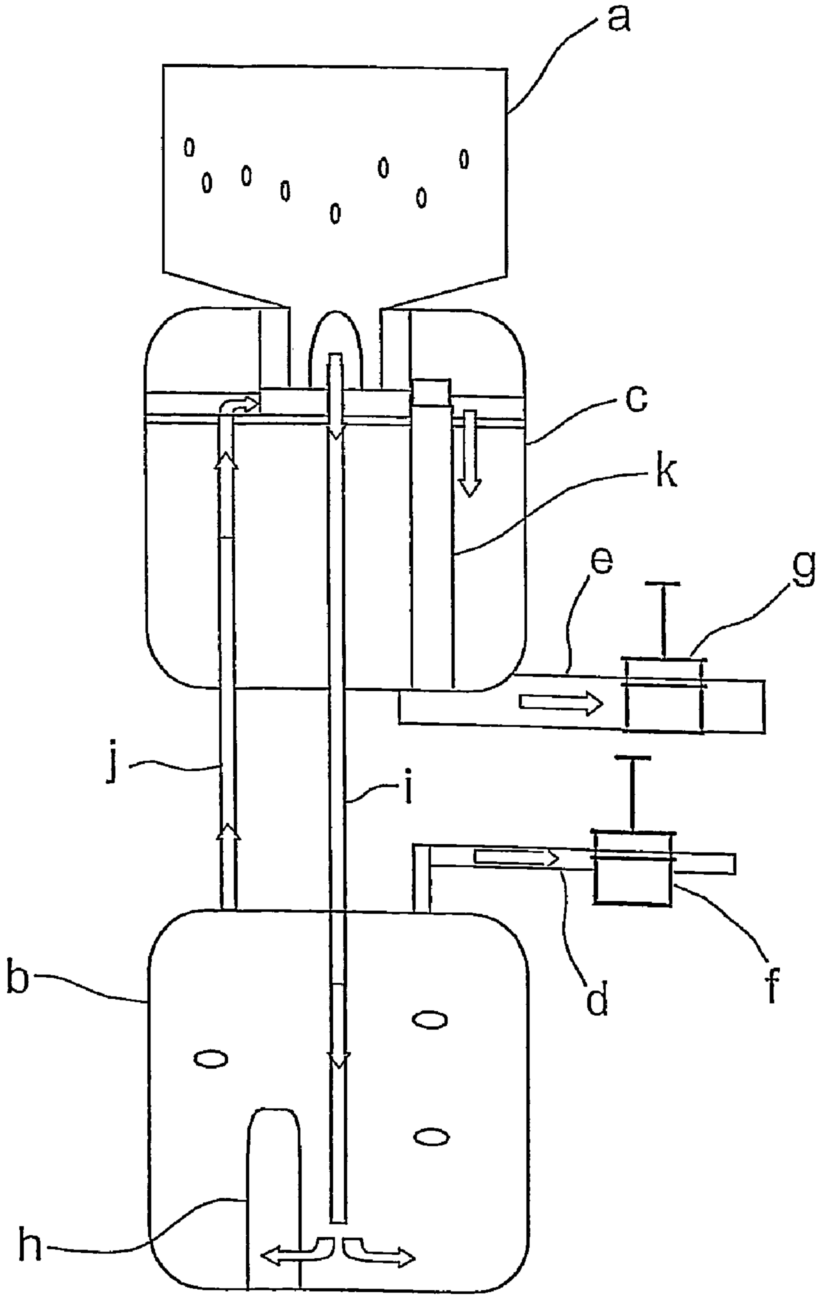
FIG. 5 is an explanatory diagram showing an outline configuration of a conventional drinking water server.
Figure 6:
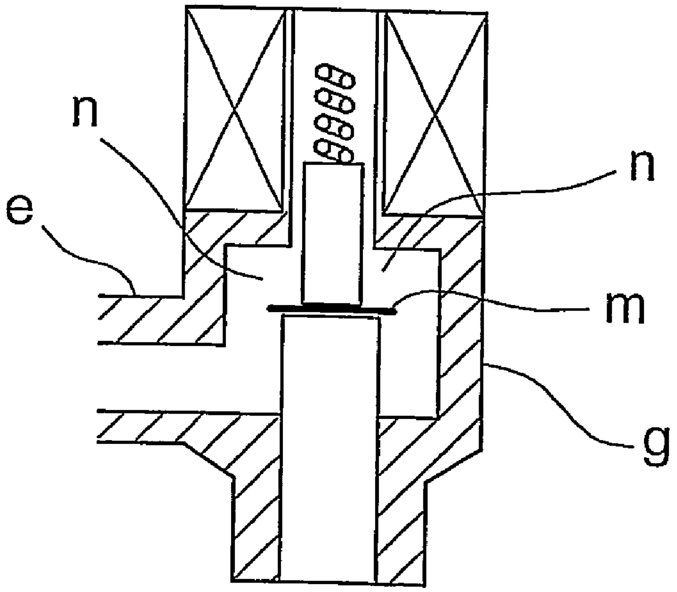
FIG. 6 is an explanatory diagram showing an outline configuration of a cold water pour valve in a conventional drinking water server.

Referring next to FIG. 4, preferred embodiment 3 of the present invention is specifically described below. Preferred embodiment 3 is similar to preferred embodiment 1 except that the ultraviolet lamp 8 is installed from above the cold water tank 2, instead of from below the cold water tank 2, and hence the mounting structure of the ultraviolet lamp insertion pipe 61 is different from that of preferred embodiment 1. The other parts are same as in preferred embodiment 1, and common parts are identified with same reference numerals, and the description is omitted.

That is, in this preferred embodiment, as shown in FIG. 4, the upper end of the ultraviolet lamp insertion pipe 61 is opened at a position reaching up to a ceiling side 2*d* of the cold water tank 2, and its lower end is formed in a structure intersecting orthogonally with an extending direction (a horizontal direction in the shown example) of the cold water pour tube 6 and being sealed at a lower position than the cold water pour tube 6, so that the ultraviolet lamp 8 can be inserted and removed from the opening part of the ceiling side 2*d* of the cold water tank 2.

More specifically, a water tap 20 of tubular shape with a bottom projecting downward is disposed in the bottom side 2*b* of the cold water tank 2. This water tap 20 has a structure functioning to lead in the cold water into the cold water pour tube 6, and to hold the lower end part of the ultraviolet lamp insertion pipe 61, and is composed of a large-diameter tube part 21 for leading the cold water into the cold water pour tube 6, an insertion pipe accommodating part 22 for holding the lower end part of the ultraviolet lamp insertion pipe 61, and a taper part 23 for linking between the two.

The large-diameter tube part 21 has its inside diameter formed larger than the outside diameter of the ultraviolet lamp insertion pipe 61, and at the lower end of the large-diameter tube part 21, the cold water pour tube 6 is connected to intersect orthogonally with the large-diameter tube part 21. At the leading end of this cold water pour tube 6, same as in preferred embodiment 1, a cold water pour valve (not shown) is disposed.

The insertion pipe accommodating part 22 has its inside diameter set nearly same as the outside diameter of the ultraviolet lamp insertion pipe 61. By inserting the lower end part of the ultraviolet lamp insertion pipe 61 into this insertion pipe accommodating part 22, the ultraviolet lamp insertion pipe 61 is held in a vertical direction. The insertion pipe accommodating part 22 and the ultraviolet lamp insertion pipe 61 are held in a water-tight state, so that water may not invade between them.

This insertion pipe accommodating part 22 is configured so that the portion for emitting ultraviolet rays of the ultraviolet lamp 8 may be opposite at least to the duct of the cold water pour tube 6 when the ultraviolet lamp 8 is installed in the ultraviolet lamp insertion pipe 61. That is, the depth dimension of the insertion pipe accommodating part 22 is determined so that the ultraviolet rays emitted from the ultraviolet lamp 8 may be uniformly emitted within the duct of the cold water pour tube 6 (in the drawing, reference numeral 81 refers to a base ring of the ultraviolet lamp 8, and numeral 82 refers to a lamp main body part for emitting ultraviolet rays).

On the other hand, the upper end of the ultraviolet lamp insertion pipe 61 is opened at a position reaching up to the ceiling side 2*d* of the cold water tank 2. This opening part is preferably opened at a position higher than the ceiling side 2*d* of the cold water tank 2, but, as shown in the drawing, a lid 14 may be provided, and by opening this lid 14, an opening part may be formed in the ceiling side 2*d*. That is, the upper end opening part of the ultraviolet lamp insertion pipe 61 is determined at a height position so that at least the cold water in the cold water tank 2 may not invade into the ultraviolet lamp insertion pipe 61.

In the drinking water server of the present preferred embodiments having such configuration, when replacing the ultraviolet lamp 8, the ultraviolet lamp 8 can be inserted and removed from above the cold water tank 2.

The illustrated embodiments are merely preferred embodiments of the present invention, and the present invention is not limited to these embodiments alone, but may be changed and modified within the scope of the true spirit thereof.

For example, in the shown preferred embodiments, the cold water pour tube 6 is connected to the bottom side of the cold water tank 2, but the cold water pour tube 6 may be also provided at a lateral side of the cold water tank 2. That is, in this case, the opening part 2*c* is provided at a lateral side of the cold water tank 2. Accordingly, the cold water pour tube 6 is formed only of a straight duct main body 6*a*, not having any bent part 6*b*, and the duct main body 6*a* is connected horizontally (or obliquely downward) to a lateral side of the cold water tank 2. The ultraviolet lamp 8 is disposed oppositely to this opening part 2*c* (so that the ultraviolet rays emitted from the ultraviolet lamp 8 may be emitted into the inside of the duct main body 6*a*), and hence by using one ultraviolet lamp 8 only, both the inside of the cold water tank 2 and the inside of the cold water pour tube 6 can be sterilized.

In the preferred embodiments, the electric heater 9 is used in the hot water tank 3 for sterilized by heat, but the hot water tank 3 may be additionally provided with cooling means, so that the temperature in the tank can be lowered suddenly, and cooling by this cooling means and heating by the electric heater 9 may be alternately controlled by the control unit 4, so that the inside of the hot water tank 3 may be sterilized intermittently. By such intermittent sterilization, blasts and spores not destroyed by thermal sterilization may be sterilized securely in a short time.

In the preferred embodiments, the drinking water server has both the cold water tank 2 and the hot water tank 3, but the present invention may be also applied to a drinking water server having only a cold water tank.

INDUSTRIAL APPLICABILITY

As mentioned herein, according to the present invention, since ultraviolet rays are simultaneously emitted from one ultraviolet emitting means to both the inside of the cold water tank and the inside of the duct of the cold water pour tube, both the inside of the cold water tank and the inside of the duct of the cold water pour tube can be suppressed in generation of bacteria economically and efficiently. Moreover, since cold water does not stay in the rear part of the valve body of the cold water pour valve, generation of bacteria can be also suppressed in the cold water pour valve. As a result, the drinking water server reduced in cost and capable of serving a sanitary drinking water can be presented.

Moreover, the valve body of diaphragm type is disposed oppositely to the ultraviolet emitting means, and there is no dead angle of ultraviolet rays in the cold water pour tube form the ultraviolet emitting means up to the cold water pour valve, and generation of bacteria in these areas can be securely prevented.

The invention claimed is:

1. A drinking water server comprising a cold water pour piping for taking out cold water disposed by communicating with an opening part formed in a cold water tank, and a cold water pour valve disposed at a leading end of the cold water pour piping, wherein ultraviolet emitting means for emitting ultraviolet rays into the cold water tank is disposed in the cold water tank, through the opening part and in the cold water pour piping, and a duct of the cold water pour piping is formed straightly, and a diaphragm type valve body for clogging the leading end of the cold water pour piping is used as a valve body for the cold water pour valve.

2. The drinking water server of claim 1, wherein the opening part is formed in the bottom side of the cold water tank, and the cold water pour piping communicating with this opening part is disposed horizontally or obliquely downward by way of a bent part, and the ultraviolet emitting means is disposed to reach the bottom side of the bent part from the inside of the cold water tank by way of the opening part.

3. The drinking water server of claim 2, wherein the ultraviolet emitting means is composed of a bar-shaped ultraviolet lamp, and an ultraviolet lamp insertion port is provided in the bottom side of the bent part.

4. The drinking water server of any one of claims 1 to 3, wherein the diaphragm type valve body is disposed oppositely to the ultraviolet emitting means.

5. The drinking water server of claim 4, wherein the diaphragm type valve body has a resistance to ultraviolet rays at least in a portion opposite to the ultraviolet emitting means.

* * * * *